(12) United States Patent
Hariram

(10) Patent No.: US 9,182,331 B2
(45) Date of Patent: Nov. 10, 2015

(54) MEASUREMENT OF SOLID, AEROSOL, VAPOR, LIQUID AND GASEOUS CONCENTRATION AND PARTICLE SIZE

(75) Inventor: Sham S. Hariram, Seattle, WA (US)

(73) Assignee: The Boeing Company, Chicago, IL (US)

(*) Notice: Subject to any disclaimer, the term of this patent is extended or adjusted under 35 U.S.C. 154(b) by 503 days.

(21) Appl. No.: 13/600,745

(22) Filed: Aug. 31, 2012

(65) Prior Publication Data

US 2014/0233017 A1   Aug. 21, 2014

(51) Int. Cl.
| | | |
|---|---|---|
| *G01N 21/00* | (2006.01) | |
| *G01N 15/10* | (2006.01) | |
| *G01N 1/26* | (2006.01) | |
| *G01N 15/02* | (2006.01) | |
| *G01N 15/06* | (2006.01) | |
| *G01N 15/14* | (2006.01) | |

(52) U.S. Cl.
CPC .............. *G01N 15/1031* (2013.01); *G01N 1/26* (2013.01); *G01N 15/0255* (2013.01); *G01N 15/0656* (2013.01); *G01N 15/14* (2013.01); *G01N 2015/0693* (2013.01); *G01N 2015/1486* (2013.01)

(58) Field of Classification Search
USPC ..................................................... 356/72–73
See application file for complete search history.

(56) References Cited

U.S. PATENT DOCUMENTS

| | | | |
|---|---|---|---|
| 3,393,079 A | 7/1968 | Masoero | |
| 4,179,218 A | 12/1979 | Erdmann et al. | |
| 4,381,666 A | 5/1983 | Feiertag et al. | |
| 4,818,101 A | 4/1989 | Soreide et al. | |
| 6,333,391 B1 | 12/2001 | Laycock et al. | |
| 2006/0232773 A1 | 10/2006 | Barton et al. | |
| 2008/0186489 A1* | 8/2008 | Ahn ............................. | 356/337 |

* cited by examiner

*Primary Examiner* — Abdullahi Nur

(74) *Attorney, Agent, or Firm* — Kunzler Law Group, PC

(57) ABSTRACT

A method and apparatus for measuring particle content in a stream, comprising routing the stream, via a plurality of tubes, from a plurality of sampling points where particle content concentrations are to be measured. The concentration of particle content in the stream may be measured. The measurement may be based on determination, via a sensor for example, of an electrostatic charge of the particles as the particles, and/or based on counting of a number of particles in the stream, such as using a counter tracking light emitted from a light source. The measured concentration of particle content may be analyzed to determine if it is indicative of an appropriate concentration of measured particles in the stream. The particles may comprise extinguishing and/or suppression agent particles.

22 Claims, 8 Drawing Sheets

MEASUREMENT OF SOLID, AEROSOL, VAPOR, LIQUID AND GASEOUS CONCENTRATION AND PARTICLE SIZE

FIELD

Embodiments of the invention relate to various systems in vehicles and aircraft including but not limited to fire extinguishing and/or suppression systems. More specifically, some embodiments of the invention relate to an apparatus and method for measurement of solid, aerosol, vapor, gaseous, and liquid concentrations and particle sizes of extinguishing agents.

BACKGROUND

Fire extinguishing and/or suppression systems enable fire extinguishing and suppression capabilities on commercial and military transportation vehicles, which may include as examples ships, trucks, aircraft, trains, and intermodal container systems. Fire extinguishing and/or suppression systems are among various safety measures that may be mandated and/or subject to government requirements or specifications. For example, the U.S. Department of Transportation requires various types of vehicles to incorporate such systems. The US Federal Aviation Administration (FAA) requires fire extinguishing and/or suppression systems to be present as a safety measure on aircraft to minimize risks that arise in transporting people and certain materials and articles. Such extinguishing and/or suppression systems may be used in civilian and military aircraft to suppress and extinguish a fire that may unexpectedly arise. The system also enables continuous suppression and/or inerting and is adapted to monitor and continuously apply inerting capabilities and agents within various compartments and areas of the vehicle such as an aircraft, which may contain or carry materials or articles that require or are well-suited to benefit from such continuous suppression or inerting. Such materials or articles may include, for purposes of example, fuel contained in fuel tanks, dry compartments or bays that may contain hazardous articles or fumes or vapors, or ordinance or ammunition containers.

Many, fire extinguishing and/or suppression systems, such as those installed in aircraft, include pressurized or unpressurized mixtures containing, inter alia, one or more extinguishing and/or suppression agents. The extinguishing and/or suppression agents may typically be solids (e.g., powder), aerosols, vapor, liquid, liquid particles, or gases, including clear gases with added colorants. Proper operation of fire extinguishing and/or suppression systems, and/or certification thereof, may require ensuring certain characteristics of and/or parameters associated with extinguishing and/or suppression agent(s), such as the concentration of extinguishing and/or suppression agent(s) in the system and when discharged, meet particular criteria (e.g., concentration of agents meeting certain threshold(s)). In many conventional extinguishing and/or suppression systems, measurement systems may be used and/or deployed to provide concentration reading or measurements from a source and/or a spot using a conventional individual sensor, e.g., optical sensor. For example, a conventional individual sensor obtains reading of a given concentration level of extinguisher gases and predicts extinguishing and/or suppression agent levels for an area.

There is a need for further improvements in dispensing and monitoring of extinguishment agents from conventional and traditional approaches to provide more cost effective, directed extinguishment, while maintaining extinguishment levels for a given containment area or structure profile; e.g., wing, engine compartment, cabin, fuselage, nacelle, cowl, storage area, equipment area, cockpit, cargo compartment, auxiliary power unit(s), compartment, and/or fuel tanks so as to provide a high level of protection to people and property and to either meet or exceed aircraft government standards, e.g., FAA regulations, for example, during pre-flight, in-flight, pre-certification, certification, post-certification, routine maintenance, as well as during remanufacturing and recertification of the aircraft components as will become apparent to one of skill in the art, through comparison of such systems with some aspects of the present invention as set forth in the remainder of the present application with reference to the drawings.

SUMMARY

An apparatus and/or method is provided for a measurement of solid, aerosol, vapor, liquid or gas, concentration and particle size, substantially as shown in and/or described in connection with at least one of the figures, as set forth more completely in the claims.

In one aspect, an apparatus for measuring particle content may comprise one or more tubes for routing a plurality of streams from a plurality of sampling points where particle content concentrations are to be measured. The apparatus may also comprise a measuring component configured for measuring concentration of particle content. In this regard, the measuring component may comprise at least one measurement module which may comprise at least one sensor for determining an electrostatic charge of the particles as the particles pass through the at least one sensor. For example, the at least one measurement module is configured to determine the electrostatic charge based on determining of a difference in a generated current as the particles pass through the at least one sensor.

The measuring component may comprise at least one measurement module which may comprise at least one source and at least one counter for counting a number of particles in the stream based on an emission from the one source. The at least one source comprises a fiber optic light source or a laser source, and the at least one counter is configured to count the number of particles or concentration based on scattering and/or obscuration of transmitted light or laser. Alternatively, the at least one source comprises a light source or a laser source, and the at least one counter is configured to count the number of particles based on particle image velocemetry. The apparatus may further comprise an analyzer or computing component for determining whether the measured concentration of particle content is indicative of an appropriate concentration of extinguishing and/or suppression agent in the stream.

In another aspect, a method for measuring particle content may comprise routing plurality of streams via a plurality of tubes, from a plurality of sampling points where particle content concentrations are to be measured. A concentration of particle content in the plurality of streams may be measured, with the measuring being based on one or more of counting of number of particles in the stream, obscuration and determination of an electrostatic charge of the particles. The measured concentration of particle content may then be analyzed to determine whether it is indicative of an appropriate concentration of extinguishing and/or suppression agent in the stream.

These and other advantages, aspects and novel features of the present invention, as well as details of an illustrated embodiment thereof, will be more fully understood from the following description and drawings.

The features, functions, and advantages that have been discussed can be achieved independently in various embodiments or may be combined in yet other embodiments further details of which can be seen with reference to the following description and drawings.

DETAILED DESCRIPTION

Certain embodiments of the invention may be found in a method and system for a measurement of solid, aerosol, vapor, liquid, liquid particles, or gases, concentration and particle size. Many specific details of certain embodiments of the invention are set forth in the following description as well as the drawings to provide a thorough understanding of such embodiments. One skilled in the art, however, will understand that the present invention may have additional embodiments, or that the present invention may be practiced without several of the details described in the following description. Identical reference numbers refer to similar elements throughout the drawings and written description of the invention.

A method and apparatus may be utilized measuring particle content in a plurality of streams. The plurality of streams may comprise a mixture of solid material, aerosol, liquid(s), vapor(s), air, gases, or any mixture thereof. The plurality of streams may be routed via a plurality of tubes, from a plurality of sampling points where particle content concentrations are to be measured. The 'plurality of tubes' may comprise any appropriate tubes, ducts, conduits, pipes, or like objects, and/or any combination thereof. In some instances, the tubes may be configured to be substantially equal in length. Also, in some instances, at least some of the tubes may be interconnected to a manifold, which may be combined with or attached to a vacuum pump for creating vacuum to cause the routing of the stream.

The concentration of particle content in the stream may be measured, such as via a measurement module. The measurement may be based on determination, via one or more sensors for example, of an electrostatic charge of the particles as the particles, and/or based on counting of a number of particles in the stream, such as using a counter tracking a particular emission, from a corresponding emission source, which may enable detecting and/or identifying the measured particles or by obscuration of light by the particle stream. The measured concentration of particle content may be analyzed to determine if it is indicative of an appropriate concentration of measured particles in the stream (e.g., meeting required concentration, whether as precise value(s) or as being within particular range, for certain substance(s), such as extinguishing and/or suppression agent(s), as mandated by, for example, regulatory guidelines—such as by the FAA regulations for certification purposes).

The stream may be routed from fire extinguishing and/or suppression system(s) or discharges thereof, which may be placed anywhere in an aircraft or other applications whether in confined or unconfined spaces such as, but not limited to cockpit area, aircraft passenger area, aircraft cargo area, auxiliary power unit(s) area, accessory compartments, wings, fuel tanks, and/or aircraft engine nacelles. The particles may comprise but not be limited to particles of extinguishing and/or suppression agent(s). In this regard, the particles or extinguishing and/or suppression agent(s) may comprise solid agent(s), vapor, liquid, liquid particles, or gases and/or aerosol agent(s). The particles may be electrostatically charged and the electrostatic charge may be determined based on detection and/or calculation of a difference in a generated current as the particles pass through the sensor(s).

The output(s) of counting of the number of the particles, obscuration levels and/or determining of the electrostatic charge of the particles may be provided to a computer or analyzer, which may be configured to provide a reading based thereon, for enabling calculation the concentration of particle content and/or the determination of whether the particle count, obscuration or electrostatic charge is indicative of an appropriate concentration (e.g., meeting required concentration, whether as precise value(s) or as being within particular range, for certain substance(s), such as extinguishing and/or suppression agent(s), as mandated by, for example, regulatory guidelines—such as by the FAA regulations for certification purposes). The measuring of concentration of particle content may be repeated, on-demand or at a given frequency. The emission source may comprise a light source, a fiber optic light source, and/or a laser source, and the counter may be configured to count the number of particles based on, particle image velocemetry and/or scattering or obscuration of emitted light or laser.

As utilized herein the terms "circuits" and "circuitry" refer to physical electronic components (i.e. hardware) and any software and/or firmware ("code") which may configure the hardware, be executed by the hardware, and or otherwise be associated with the hardware. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the terms "block" and "module" refer to functions than can be performed by one or more circuits. As utilized herein, the term "exemplary" means serving as a non-limiting example, instance, or illustration. As utilized herein, the term "e.g.," introduces a list of one or more non-limiting examples, instances, or illustrations.

Figure 1A:
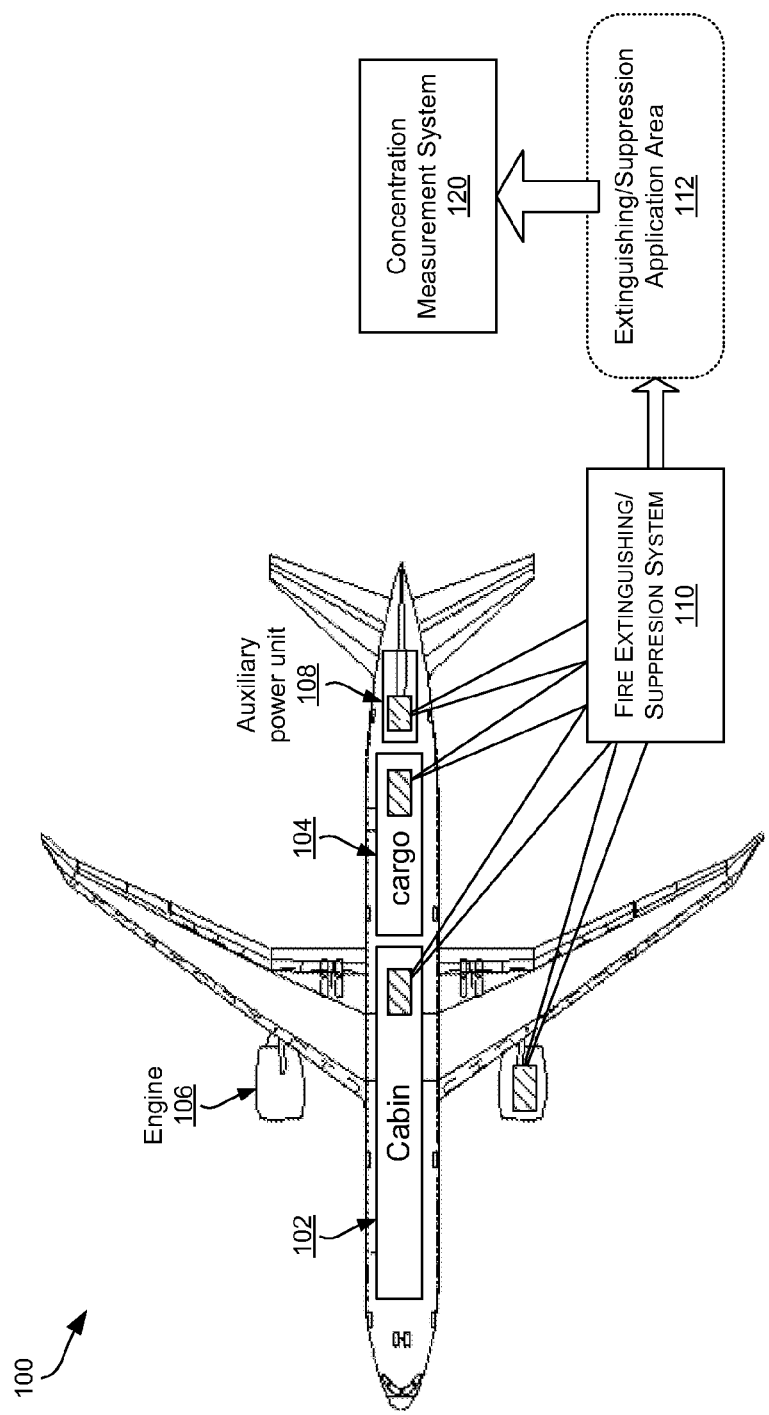
FIG. 1A is a diagram illustrating an aircraft comprising fire extinguishing and/or suppression components in one or more sections or areas of the aircraft.

FIG. 1A is a diagram illustrating an aircraft comprising fire extinguishing and/or suppression components in one or more sections or areas of the aircraft. Referring to FIG. 1A, there is shown an aircraft 100. In this regard, the aircraft 100 may be a military or a civilian aircraft, and may be utilized, in some instances, to carry people (crew and/or passengers) and/or cargo. The invention is not limited, however, to any particular aircraft, and may apply similarly to other types of aerial, marine, ground transportation, space equipment, or ground structures.

The aircraft 100 may comprise, for example, a cabin compartment 102, which may be used by crew and/or passenger(s) and/or carriage of cargo; a cargo compartment (upper and/or lower) 104, which may be utilized for cargo transported via the aircraft 100; one or more engines 106, which may comprise any available engines used in aircrafts (e.g., jet engine, prop engines, and the like); and/or one or more auxiliary power unit(s) 108. The invention is not limited, however, to any particular type of engines or to any particular compartment but to an aircraft as a whole that includes any and all enclosed and unenclosed spaces and equipment.

The aircraft 100 may incorporate fire extinguishing and/or suppression system(s). For example, the cabin compartment 102, the cargo compartment 104, the one or more engines 106, and/or the one or more auxiliary power unit(s) 108 may each incorporate a fire extinguishing and/or suppression system 110. The fire extinguishing and/or suppression system 110 may comprise suitable physical components, circuitry, logic, interfaces, and/or code for extinguishing fires that may start or reach, or keep the fires suppressed in, each of the areas of the aircraft 100 in which an instance of the fire extinguishing and/or suppression system 110 is installed. Fire suppression may be applied in areas (e.g., the cargo compartment 104) where the focus is keeping the fire suppressed long enough and not allowed to migrate to other areas to allow a safe landing at the nearest suitable airport.

On the other hand, immediate fire extinguishing may be required in other areas, such as the engine(s) 106, and as such the fire extinguishing and/or suppression system 110 may be configured to apply fire extinguishing and cause fire extinguishment immediately whenever the system is triggered (e.g., smoke or fire is detected). In addition to any physical components required for extinguishing and/or suppression fires, the fire extinguishing and/or suppression system 110 may also comprise suitable circuitry, logic, interfaces, and/or code for controlling and/or managing operations and/or functions of the fire extinguishing and/or suppression system 110. In some instances, the fire extinguishing and/or suppression system 110 may be manually operated (e.g., by a person).

Alternatively, the fire extinguishing and/or suppression system 110 may be automatically operated. In this regard, the fire extinguishing and/or suppression system 110 may comprise, or be coupled to sensor(s) which may detect for particular conditions (e.g., example, smoke, flames, temperature or increase in CO and/or $CO_2$ or a combination of any) that may trigger operations of the fire extinguishing and/or suppression system 110. The fire extinguishing and/or suppression system 110 may also comprise suitable circuitry, logic, interfaces, and/or code for controlling and/or managing operations and/or functions of the fire extinguishing and/or suppression system 110 measurement of solid, aerosol, vapor, liquid and gaseous concentration and particle size.

In some instances, the fire extinguishing and/or suppression system 110 may include pressurized or unpressurized mixture containing, inter alia, one or more extinguishing and/or suppression agents that are particularly pertinent to the fire extinguishing and/or suppression functions or operations. In this regard, fire extinguishing and/or suppression may include releasing a stream of the mixture from the fire extinguishing and/or suppression system 110, such as in a controlled manner or uncontrolled manner, based on the location of the fire, temperature, smoke and/or CO or $CO_2$ for example.

The extinguishing and/or suppression agents may include solid agents (e.g., powder), vapor, liquid, liquid particles, gas, aerosol agents or a mixture of any. In some instances, the fire extinguishing and/or suppression system 110 may also incorporate inerting (particularly continuous inerting) capabilities. In this regard, continuous inerting may comprise continuous monitoring and application of inerting in certain areas of particularly high risk of fire (e.g., fuel tank and/or dry bays, or ammunition areas in military aircraft), to ensure that inerting concentrations of particular agent(s) are not allowed to drop below certain level(s).

In an aspect of the invention, measurement of concentration of certain particle and/or gas content may be needed. In this regard, in many instances aircraft or particular components or areas thereof (including components or areas where fire extinguishing and/or suppression systems may be installed) may have to be certified (e.g., by particular regulatory or administrative government agency, such as the FAA) as fulfilling current applicable requirements, which may pertain to overall airworthiness, safe conduct, and/or proper operation, before such aircrafts are allowed to be used. Thus, aircraft certification may entail certifying that fire extinguishing and/or suppression systems installed in aircraft, or operations thereof, meet applicable requirements. For example, proper operations of fire extinguishing and/or suppression system 110, and/or certification thereof, may require ensuring that the concentration of extinguishing and/or suppression agent(s) in the system meets particular criteria (e.g., minimum threshold for proper operation).

In this regard, measurement of the concentration of solids, aerosols (particles), liquids, vapors and/or gases in mixture contained in fire extinguishing and/or suppression system 110 may be required for certification testing of extinguishing and/or suppression agents utilized in certain areas of an aircraft, such as aircraft 100, as part of the overall certification (of the aircraft), and/or for any re-testing of fire extinguishing and/or suppression system 110 thereafter. Concentration of extinguishing and/or suppression agents may be measured during certification process using dedicated measurement systems or may be measured as a part of a dedicated system on an aircraft. In this regard, currently available measurement systems used in measuring quantities or concentration of extinguishing and/or suppression agent(s) present in particular areas or systems of aircrafts are typically spot based measurement systems.

In contrast, a spot measurement system may provide concentration reading or measurement from single source and/or at single spot (i.e., providing only single spot reading). One conventional source measurement system has an open air type sensor placed at a particular area to obtain reading of a specific chemical or a chosen concentration of extinguishing and/or suppression agent at one local spot, e.g., such as based on measuring of opaqueness and/or other analysis thereof. Other conventional measurement systems may include open air based systems, thus performing the reading of the mixture being measured (e.g., containing extinguishing and/or suppression agent) in open air, after it is released; thus; the reading being potentially affected by immediate atmospheric effects.

Accordingly, in various embodiments of the invention, a concentration measurement system 120 may be utilized to perform concentration measurements, such as with respect to the fire extinguishing and/or suppression system 110, in a manner that may allow reading measured substance (e.g. extinguishing and/or suppression agents) from multiple sources and/or at multiple spots and/or areas; with measurement being performed using multiple and/or different measuring components (e.g., sensors), such as to enable multiple (redundant or separate) measurements; and/or with the reading(s) and/or measurement(s) being done in a controlled manner (e.g., being performed in contained and controlled space rather than in open air). In this regard, the concentration measurement system 120 may be used to measure concentration of certain contents (e.g., particles corresponding to extinguishing and/or suppression agents in the fire extinguishing and/or suppression system 110 for example), and/or to perform any required analysis thereof, to enable determining whether measured concentrations are indicative of appropriate concentrations and/or levels.

For example, during certification of the aircraft 100, the concentration measurement system 120 may be used to measure concentration of extinguishing and/or suppression agent(s) in application area(s) 112, where extinguishing and/or suppression mixtures may be released from the fire extinguishing and/or suppression system 110. In other words, the application area(s) 112 may correspond to extinguishing and/or suppression areas. The application area(s) 112 may comprise to areas in the cabin compartment 102, the cargo compartment 104, the engine(s) 106, and/or the auxiliary power unit(s) 108. In some instances, the concentration measurement system 120 may be utilized to provide concentration measurements (e.g., of extinguishing and/or suppression agent(s)) for other than certification purposes.

For example, the concentration measurement system 120 may also be utilized for providing measurement during pre-flight tests or checks, or even in-flight. In this regard, the concentration measurement system 120 may be used to measure, for example, concentration of extinguishing and/or suppression agent(s) in streams released from the fire extinguishing and/or suppression system(s) 110 before commencement of flights and/or during flight. This may be done, for example, in instances where there may be increased risk of fire, such as due to the mission or configuration of the aircraft 100 and/or the cargo carried therein.

The concentration measurement system 120 may be a portable device, which may be moved such as to allow performing the necessary measurement at different application areas 112. Thus, when used for certification purposes, the concentration measurement system 120 may be simply brought to the areas where concentration measurements need be performed (e.g., concentration of extinguishing and/or suppression agent(s) in extinguishing and/or suppression mixtures released from fire extinguishing and/or suppression system(s) 110). In some instances, however, the concentration measurement system 120 may be incorporated into and/or kept within the aircraft 100, such as when the concentration measurement system 120 is utilized for pre-flight or in-flight testing purposes.

In this regard, the concentration measurement system 120 may still be utilized in such scenarios a portable system (e.g., being applied and/or used by crewmember(s) bringing the concentration measurement system 120 to the areas where measurements are to be performed). Alternatively, the concentration measurement system 120 may implemented as a fixed component of the aircraft 100, being installed, for example, predetermined application area(s) 112, and/or being configured for manual or remote operation when measurements are needed. Accordingly, measurements may be on performed while the aircraft is on the ground, in flight and/or during any operation of the aircraft.

Figure 1B:
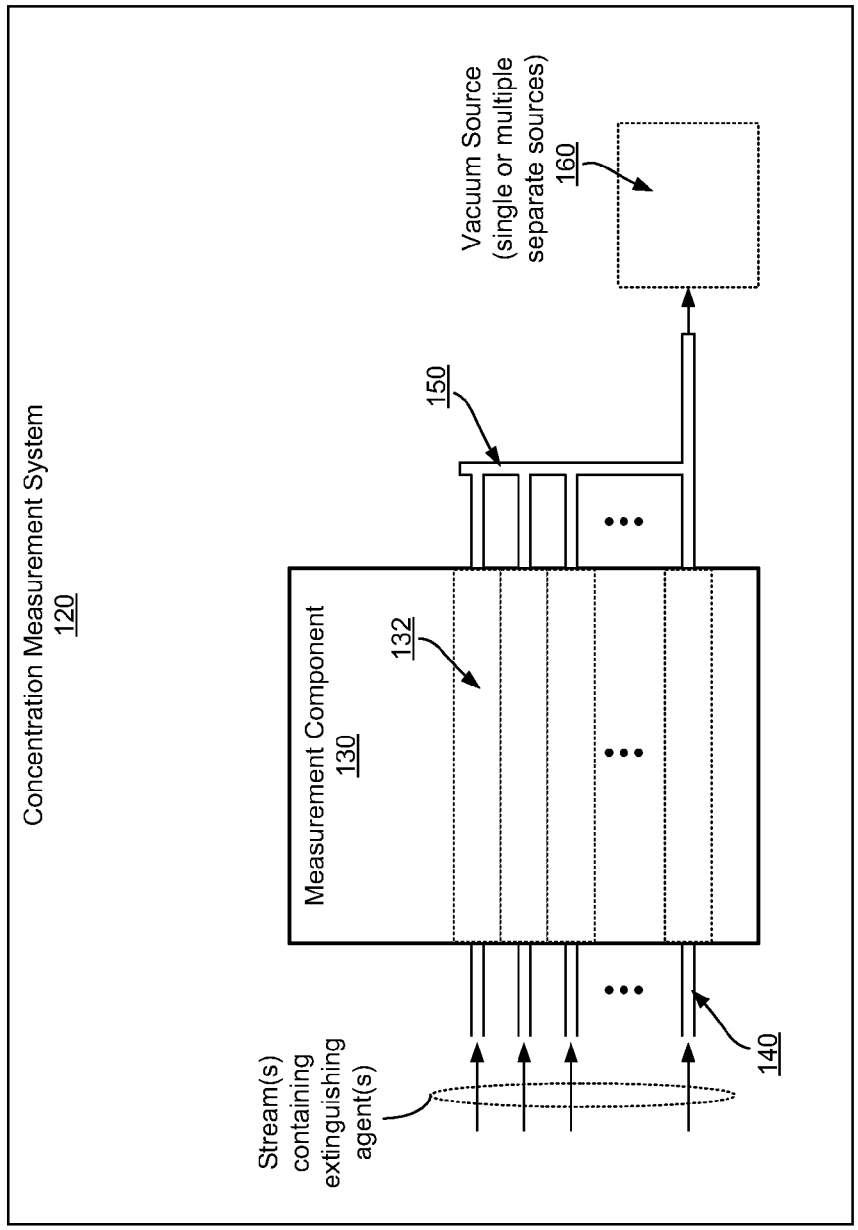
FIG. 1B is a diagram illustrating a concentration measurement system that may be used in measuring concentration of extinguishing and/or suppression agent(s) of fire extinguishing and/or suppression components in an aircraft.

FIG. 1B is a diagram illustrating a concentration measurement system that may be used in measuring concentration of extinguishing and/or suppression agent(s) of fire extinguishing and/or suppression components in an aircraft. Referring to FIG. 1B, there is shown the concentration measurement system 120 of FIG. 1A.

The concentration measurement system 120 may comprise suitable components, circuitry, logic, interfaces, and/or code that may be operable to measure concentration of certain contents (e.g., particles corresponding to extinguishing and/or suppression agents in the fire extinguishing and/or suppression system 110 for example). For example, the concentration measurement system 120 may comprise a plurality of in-flow tubes 140, a measurement component 130, and plurality of out-flow tubes 150. In this regard, the plurality of in-flow tubes 140 may be used for routing a plurality of streams, such as of the fire extinguishing and/or suppression mixture (containing particles corresponding to the pertinent extinguishing and/or suppression agents), which may be generated and/or stored in the fire extinguishing and/or suppression system 110, to allow measuring particle content concentrations.

In this regard, the plurality of in-flow tubes 140 may enable routing the plurality of (mixture) streams from a plurality of sampling points where particle content concentrations are to be measured. In other words, rather than providing spot sampling at only single point(s), the concentration measurement system 120 may allow simultaneous reading of concentrations at multiple points.

This may allow determining different concentrations associated with each of the different spots from which the mixture streams are drawn. For example, sampling multiple spots at the same time may enable certifying presence of different acceptable concentrations of extinguishing and/or suppression agent(s)—i.e., measuring (to determine) that concentration of pertinent extinguishing and/or suppression agent(s) may be 2% in spot A, 5% in spot B, and 10% in spot C. Alternatively, in some instances, the use of multiple in-flow tubes 140 may be used to performed concurrent, multiple measurements of the same spot. In this regard, in some instances some of the in-flow tubes 140 may be used to draw mixture stream(s) from the same spot, to increase the volume of the measured mixture and/or to enable performing multiple measurements associated with the same spot.

The measurement component 130 may be configured for performing the necessary measurements of concentration of particle content in the plurality of streams, which may be routed via the plurality of in-flow tubes 140. In this regard, measurement component 130, which may comprise a plurality of measuring modules 132 for performing the necessary measurements of concentration of particle content in the plurality of streams, which may be routed into the plurality of measuring modules 132 via the plurality of in-flow tubes 140. The plurality of out-flow tubes 150 may be configured for routing the mixture streams out of the measurement component 130, after completion of measuring particle content concentrations therein, via the plurality of measuring modules 132.

In this regard, the use of plurality of in-flow tubes 140 and the plurality of out-flow tubes 150 may allow forcing the mixture (streams thereof) being measured into the measurement component 130, to enable performing the concentration measurements in enclosed and controlled environment rather than in open air. Furthermore, various mechanisms may be utilized to enable and/or regulate the routing of the mixture stream through the concentration measurement system 120, via the plurality of in-flow tubes 140 and the plurality of out-flow tubes 150.

Various mechanisms may be utilized (i.e., in the measuring modules 132) for measuring the concentration of certain extinguishing and/or suppression agents. For example, the plurality of measuring modules 132 may be configured to measure concentration of particle content in the routed mixture stream based on counting of a number (total or sample size) of particles in the routed stream and/or based on detection and/or determination of electrostatic charge of the measured particles. The various measuring techniques are described in more details in at least some of the following figures.

In some implementations, each of the plurality of measuring modules 132 may be configured to implement and/or utilize the same measurement mechanism. In other words, all of the plurality of measuring modules 132 would be configured to apply the same type of measurement technique, to enable consistent measuring. In other instances, however, the plurality of measuring modules 132 may be configured to implement and/or utilize different measurement mechanisms described in the following figures.

In some implementations, the measurement component 130 may be configured to determine additional characteristics (in addition to concentration) of particle content in the routed mixture stream, such as particle size for example. In some instances, an analyzer or computing component (not shown) may be integrated into or coupled to the measurement component 130 for analyzing the measurement obtained via the measuring modules 132. For example, such analyzer or computing component may be operable to determine whether measured concentration of certain particle content may be indicative of an appropriate concentration of extinguishing and/or suppression agent in the mixture stream (e.g., meeting required concentration, whether as precise value(s) or as being within particular range, of the extinguishing and/or suppression agent(s), as mandated by, for example, regulatory guidelines—such as by the FAA regulations for certification purposes).

In some instances, the concentration measurement system 120 may be configured to account for, when analyzing and/or processing measurements performed thereby, factors and/or variations relating to the measured mixtures and/or the environment where measurements are performed. For example, the analyzer or computing component described above may be configured to account for, when making determinations relating to the measured concentrations, differences in temperature where the mixture streams are drawn from (e.g., account for different acceptable concentrations that may be needed for different extinguishing and/or suppression areas, such as in the cockpit vs. engines, different parts of the extinguishing and/or suppression area, such as outside vs. inside turbine, and/or different conditions of the same extinguishing and/or suppression area, such as hot engine vs. cold engine).

In some implementations, each of the in-flow tubes 140 and/or each of the out-flow tubes 150 may be configured to be substantially equal in length. Various mechanisms may be utilized to enable and/or regulate the routing of the mixture stream through the concentration measurement system 120. For example, the out-flow tubes 150 may be interconnected to a manifold, which may be attached to a vacuum pump (160) for creating a vacuum at the out-flow side for forcing the routing of the mixture streams into the plurality of measuring modules 132, via in-flow tubes 140.

Alternatively, each (or subsets) of the out-flow tubes 150 may connect to separate vacuum sources (e.g., vacuum pumps). In some instances, the flow rates of the different mixture streams (e.g., in each of the in-flow tubes 140 and/or the corresponding one of the out-flow tubes 150) may differ. In this regard, the flow rates may be configured separately and/or adaptively, such as in accordance with varying flow requirements of the particular measurements being performed in the plurality of measuring modules 132, due to varying measuring techniques being implemented by the plurality of measuring modules 132 for example.

Figure 2:
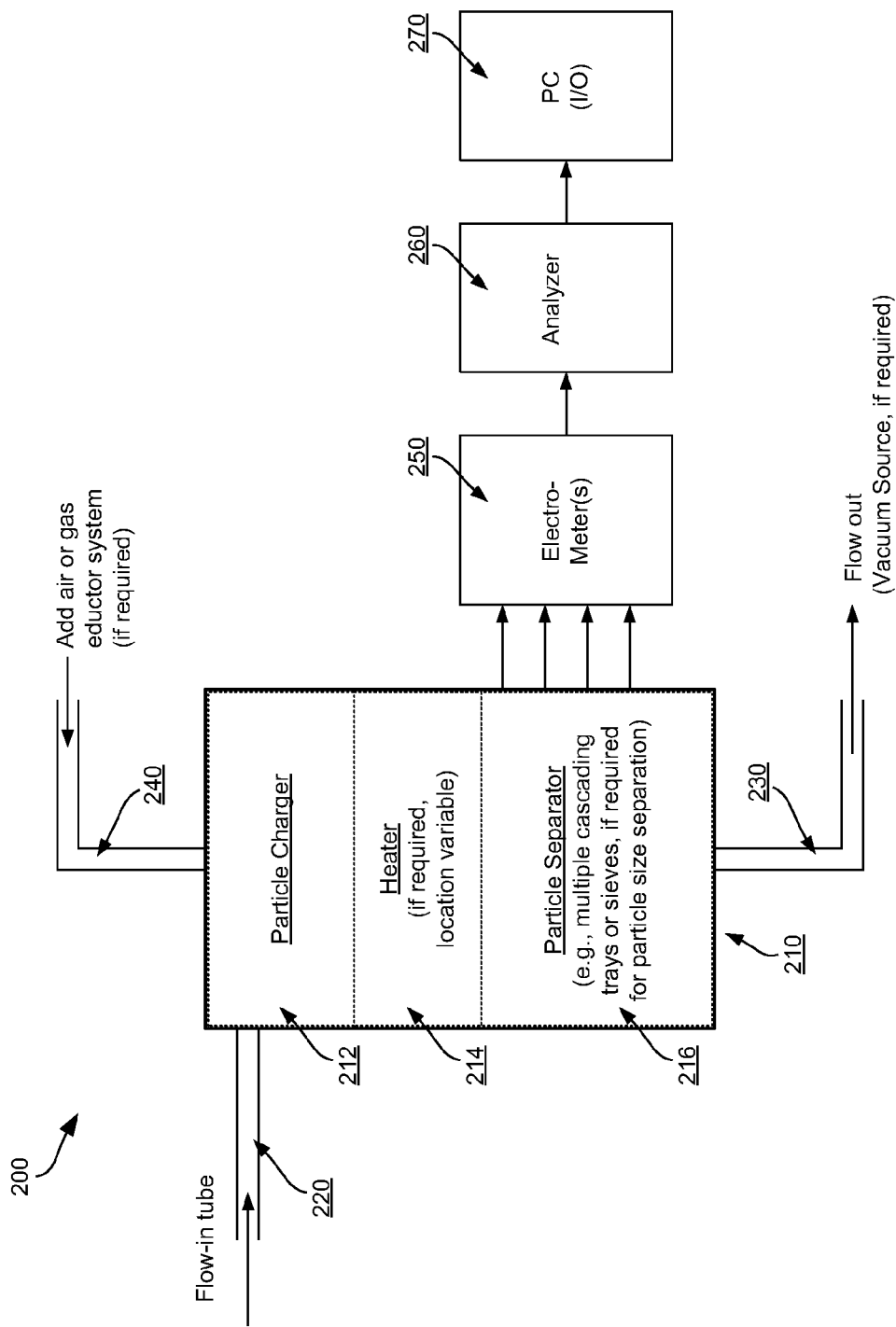
FIG. 2 is a diagram illustrating a particle concentration measurement module that may be utilized in determining concentration of particular agents in a stream using charged particles techniques, in accordance with an advantageous embodiment of the invention.

FIG. 2 is a diagram illustrating a particle concentration measurement module that may be utilized in determining concentration of particular agents in a stream using charged particles techniques, in accordance with an advantageous embodiment of the invention. Referring to FIG. 2, there is shown a concentration measurement system 200.

The concentration measurement system 200 may correspond to, and/or may be utilized to implement functions and/or operations associated with one of the measuring modules 132 of the concentration measurement system 120 of FIG. 1. In this regard, the concentration measurement system 200 may comprise suitable components, circuitry, logic, interfaces, and/or code that may be operable to generate and/or obtain measurement concentration of particle content in streams (e.g., particles corresponding to extinguishing and/or suppression agents in the fire extinguishing and/or suppression stream), and/or to perform any required analysis thereof, to enable determining whether measured concentrations are indicative of appropriate concentrations and/or levels.

The concentration measurement system 200 may be configured to measure concentrations of particle content based on charged particle method. In this regard, in accordance with the charged particle method, amount and/or concentration of particles may be determined by detecting particular charge value or level that uniquely identified the pertinent particle. The detected charge (level) may correspond to the particles' natural charge and/or to charge specifically applied to the pertinent particles for identification thereof.

The concentration measurement system 200 may comprise, for example, one or more in-flow tubes 220 and one or more out-flow tubes 230, for use in routing the stream containing the particle through a measurement module 210. The in-flow tubes 220 and/or the out-flow tubes 230 may be used to facilitate the routing of mixture stream through the measurement module 210, substantially as described with respect to the in-flow tubes 140 and/or the out-flow tubes 150 of FIG. 1. In some instances, an eductor tube 240 may also be attached to the measurement module 210, to add and/or inject calibrated gases and/or air to propel charged particles of the material or it may use a vacuum system to pull in the charged particles of the material without dilution.

The measurement module 210 may comprise particle charger 212, a particle heater 214, and particle separator 216. The particle charger 212 may be configured to charge particles (e.g., applying electrostatic and/or unipolar charges) in the routed stream, received via the in-flow tube(s) 220. In this regard, the particle charger 212 may be operable to apply particular charge to certain (type) of particles. For example, the particle charger 212 may be operable to apply unique charges to fire extinguishing and/or suppression agents' particles. The charged particles may then be forced through the particle heater 214 (and subsequently the particle separator 216).

In some instances, the charged particles may be propelled and/or forced using calibrated gases and/or air injected via the eductor tube 240. The particle heater 214 may be operable to heat the charged particles, which may ease separation of the particles and/or detection or measurement of charges thereof. The particle separator 216 may be configured to separate particles based on one or more physical attributes, such as particle size for example. The particle separator 216 may comprise, for example, a particle classifier that uses a cascade strainer to separate particles into plurality of classes of increasing particle sizes. The charged particles may then be processed via one or more electrometers 250, which may be configured to detect and/or measure electro charges, such as electrostatic charges of the particles.

The concentration measurement system 200 may also comprise an analyzer 260 and/or a computer 270. In this regard, the analyzer 260 and/or the computer 270 may be configured to analyze, process, and/or generate certain data, such as data related to measurement of particle content or concentrations thereof. For example, the charge detection measurements, as determined via the electrometer(s) 250, may be provided to the analyzer 260 and/or the computer 270, for analysis and/or processing thereof. In this regard, the analyzer 260 and/or the computer 270 may be wired to or wirelessly connected to measurement module 210 and/or the electrometer(s) 250.

The analyzer 260 and/or the computer 270 may be configured to determine particle size and/or concentration based on, for example, the charge detection measurements. Furthermore, the analyzer 260 and/or the computer 270 may be configured to determine whether the measured concentration and/or characteristics (e.g., particle size) of particle content in the routed stream may be indicative of appropriate levels of the particle (e.g., meeting required concentration or certain characteristics, whether as precise value(s) or as being within particular range, for certain substance(s), such as extinguishing and/or suppression agent(s), as mandated by, for example, regulatory guidelines—such as by the FAA regulations for certification purposes). This may enable, for example, confirming whether concentration of extinguishing and/or suppression agent(s) in fire extinguishing and/or suppression stream is acceptable.

Figure 3:
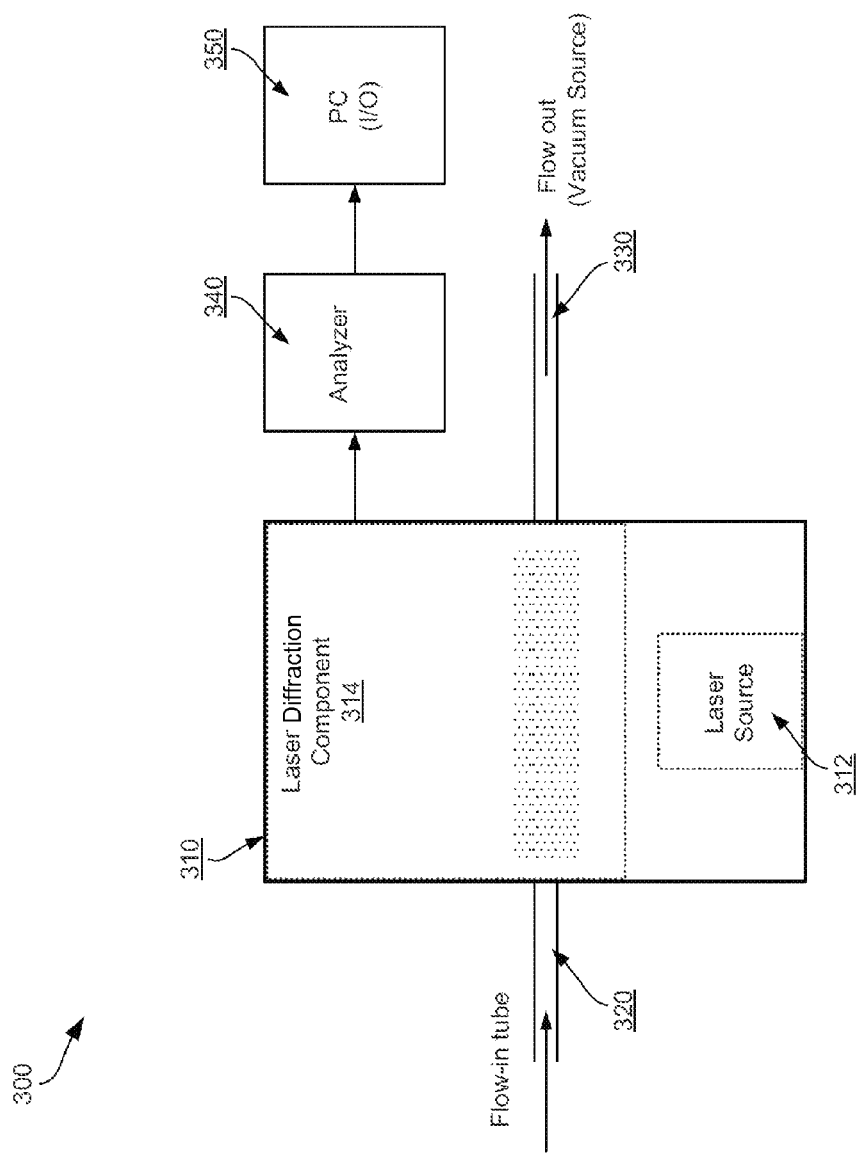
FIG. 3 is a diagram illustrating a particle concentration measurement module that may be utilized in determining concentration of particular agents in a stream using laser diffraction techniques, in accordance with an advantageous embodiment of the invention.

FIG. 3 is a diagram illustrating a particle concentration measurement module that may be utilized in determining concentration of particular agents in a stream using laser diffraction techniques, in accordance with an advantageous embodiment of the invention. Referring to FIG. 3, there is shown a concentration measurement system 300.

The concentration measurement system 300 may correspond to, and/or may be utilized to implement functions and/or operations associated with one of the measuring modules 132 of the concentration measurement system 120 of FIG. 1. In this regard, the concentration measurement system 300 may comprise suitable components, circuitry, logic, interfaces, and/or code that may be operable to generate and/or obtain measurement concentration of particle content in streams (e.g., particles corresponding to extinguishing and/or suppression agents in the fire extinguishing and/or suppression stream), and/or to perform any required analysis thereof, to enable determining whether measured concentrations are indicative of appropriate concentrations and/or levels (e.g., meeting required concentration, whether as precise value(s) or as being within particular range, of the extinguishing and/or suppression agent(s), as mandated by, for example, regulatory guidelines—such as by the FAA regulations for certification purposes).

The concentration measurement system 300 may be configured to measure concentrations of particle content based on counting of particle, which may be performed by uniquely identifying (and thus counting) the target particles. For example, the concentration measurement system 300 may be operable to implement particle counting based on laser or light diffraction, such as by measuring interactions of particles and incident and/or scattered laser or light, to enable determining particular characteristics associated with the material (e.g., size of certain types of particles), and/or calculating distribution or concentration of the material travelling through the tube in real time, or at any time or time frequency.

The concentration measurement system 300 may comprise, for example, one or more in-flow tubes 320 and one or more out-flow tubes 330, for use in routing the stream containing the particle through a measurement module 310. The in-flow tubes 320 and/or the out-flow tubes 330 may be used to facilitate the routing of mixture stream through the measurement module 310, substantially as described with respect to the in-flow tubes 140 and/or the out-flow tubes 150 of FIG. 1.

The measurement module 310 may comprise laser or light source 312. The laser or light source 312 may be configured to emit laser or light to enable identifying particular particles, such as in the routed stream, received via the in-flow tube(s) 320. In this regard, the laser or light source 312 may be operable to emit laser or light that may have particular characteristics specifically configured to interact with certain (types of) or particle or to do so (that is interact) in particular manner. For example, the interaction may comprise unique form of scattering (e.g., at particular angle and/or with particular change in characteristics, such as particular change in wavelength). Accordingly, based on measurement of the interactions between the emitted laser or light and the target particles, particles may be counted and/or certain characteristics thereof (e.g., size) may be determined.

The concentration measurement system 300 may also comprise an analyzer 340 and/or a computer 350. In this regard, the analyzer 340 and the computer 350 may be substantially similar to the analyzer 260 and the computer 270, respectively, as describe with respect to FIG. 2. The analyzer 340 and/or the computer 350 may be configured to determine particle count and/or size, and/or concentration of the particle content based on, for example, the laser or light interaction related measurements.

Furthermore, the analyzer 340 and/or the computer 350 may be configured to determine whether the measured concentration and/or characteristics (e.g., size) of particle content in the routed stream may be indicative of appropriate levels of the particle (e.g., meeting required concentration or certain characteristics, whether as precise value(s) or as being within particular range, for certain substance(s), such as extinguishing and/or suppression agent(s), as mandated by, for example, regulatory guidelines—such as by the FAA regulations for certification purposes). This may enable, for example, confirming whether concentration of extinguishing and/or suppression agent(s) in fire extinguishing and/or suppression stream is acceptable.

Figure 4:
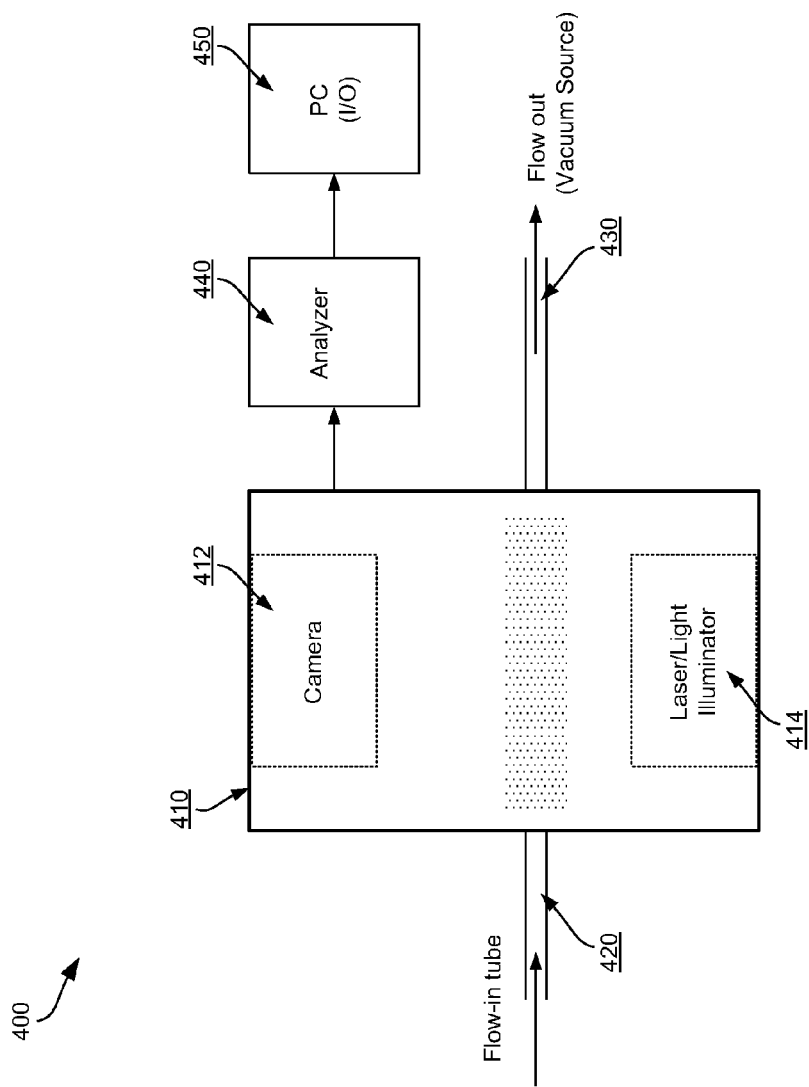
FIG. 4 is a diagram illustrating a particle concentration measurement module that may be utilized in determining concentration of particular agents in a stream using particle image velocemetry (PIV) based techniques, in accordance with an advantageous embodiment of the invention.

FIG. 4 is a diagram illustrating a particle concentration measurement module that may be utilized in determining concentration of particular agents in a stream using particle image velocimetry (PIV) based techniques, in accordance with an advantageous embodiment of the invention. Referring to FIG. 4, there is shown a concentration measurement system 400.

The concentration measurement system 400 may correspond to, and/or may be utilized to implement functions and/or operations associated with one of the measuring modules 132 of the concentration measurement system 120 of FIG. 1. In this regard, the concentration measurement system 400 may comprise suitable components, circuitry, logic, interfaces, and/or code that may be operable to generate and/or obtain measurement concentration of particle content in streams (e.g., particles corresponding to extinguishing and/or suppression agents in the fire extinguishing and/or suppression stream), and/or to perform any required analysis thereof, to enable determining whether measured concentrations are indicative of appropriate concentrations and/or levels. The concentration measurement system 400 may be configured to measure concentrations of particle content based on counting of particle. In this regard, the concentration measurement system 400 may be operable to implement particle counting using velocemetry based techniques.

For example, the concentration measurement system 400 may implement particle image velocemetry (PIV), using lasers and/or optics for example. Alternatively, laser Doppler velocemetry, hot wire anemometry, or particle tracking velocemetry may be used. In velocemetry based techniques, particle content may be determined by illuminating a mixture containing particles (e.g., using light or laser) so that the particle become visible, and then measuring of interactions of particles and incident and/or scattered laser or light, using a camera or similar optic recording devices, to measure and/or record data relating to velocity measurements and related properties pertaining to the mixture streams and/or to the particles contained therein. The velocity measurements may in turn be used to enable calculating particle size, and distribution or concentration of the material travelling through the tube in real time, or at any time or time frequency.

The concentration measurement system 400 may comprise, for example, one or more in-flow tubes 420 and one or more out-flow tubes 430, for use in routing the stream containing the particle through a measurement module 410. The in-flow tubes 420 and/or the out-flow tubes 430 may be used to facilitate the routing of mixture stream through the measurement module 410, substantially as described with respect to the in-flow tubes 140 and/or the out-flow tubes 150 of FIG. 1.

The measurement module 410 may comprise a laser or light source 414 and a camera 412 (or any similar light, laser, or optics capturing or recording means). The laser or light source 414 may be configured to emit laser or light to enable identifying particular particles, such as in the routed stream, received via the in-flow tube(s) 420. In this regard, the laser or light emitted by the laser or light source 414 may illuminate the particles in the routed mixture stream, to enable detecting and/or tracking particles (via the camera 412), and/or determining characteristics thereof, based on velocemetry techniques. This may then enable obtaining and/or generating velocity measurement pertaining to the (target) particles.

The concentration measurement system 400 may also comprise an analyzer 440 and/or a computer 450. In this regard, the analyzer 440 and the computer 450 may be substantially similar to the analyzer 260 and the computer 270, respectively, as describe with respect to FIG. 2. The analyzer 440 and/or the computer 450 may be configured to calculate, obtain, and/or process velocemetry related measurements, based on velocemetry data obtained via the measurement module 410, and/or to generate or derive particle count related data therefrom, which may in turn be utilized in calculating concentrations of the particle content.

In some instances, the analyzer 440 and/or the computer 450 may be configured to determine whether the measured concentration and/or characteristics of particle content in the routed stream may be indicative of appropriate levels of the particle (e.g., meeting required concentration or certain characteristics, whether as precise value(s) or as being within particular range, for certain substance(s), such as extinguishing and/or suppression agent(s), as mandated by, for example, regulatory guidelines—such as by the FAA regulations for certification purposes). This may enable, for example, confirming whether concentration of extinguishing and/or suppression agent(s) in fire extinguishing and/or suppression stream is acceptable.

Figure 5:
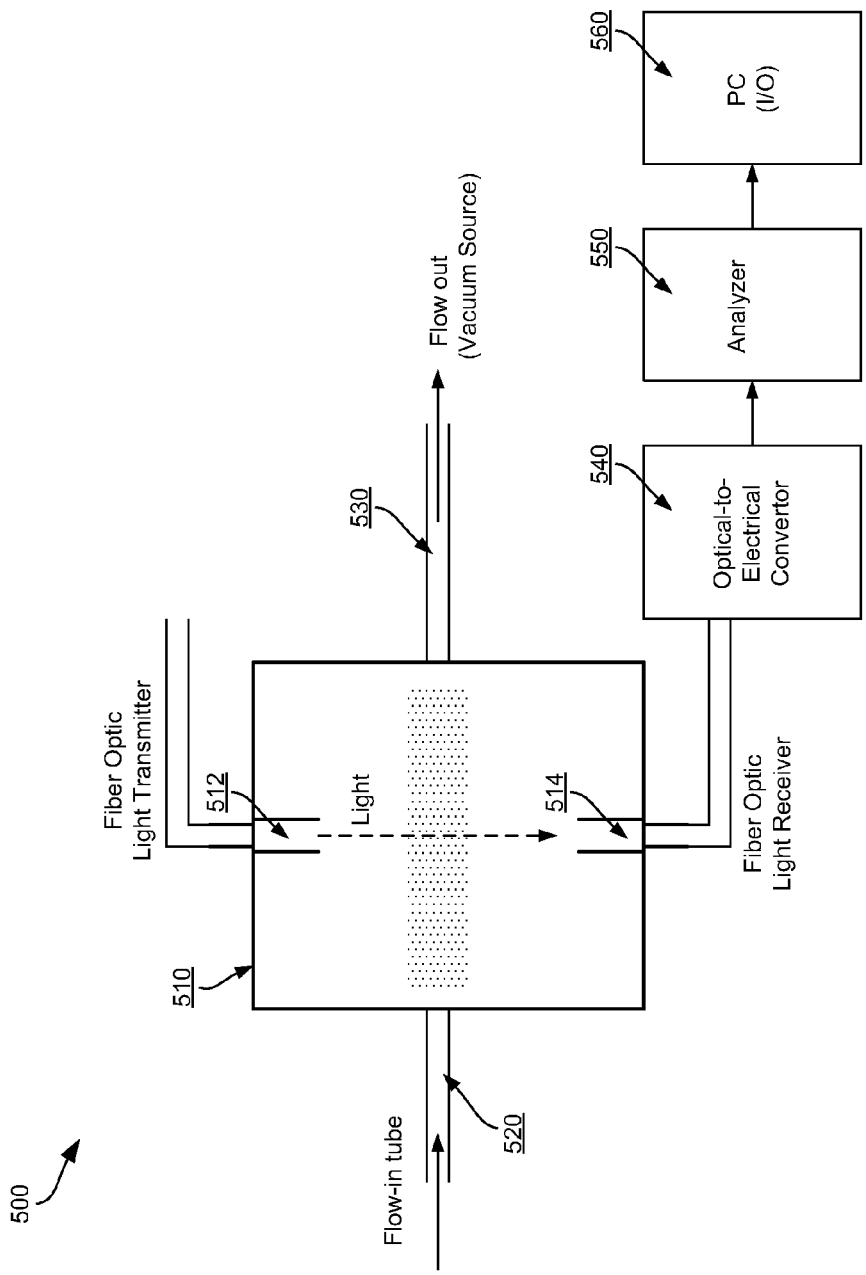
FIG. 5 is a diagram illustrating a particle concentration measurement module that may be utilized in determining concentration of particular agents in a stream based on obscuration or light scattering techniques using a fiber optic light source, in accordance with an advantageous embodiment of the invention.

FIG. 5 is a diagram illustrating a particle concentration measurement module that may be utilized in determining concentration of particular agents in a stream based on obscuration or light scattering techniques using a fiber optic light source, in accordance with an advantageous embodiment of the invention. Referring to FIG. 5, there is shown a concentration measurement system 500.

The concentration measurement system 500 may correspond to, and/or may be utilized to implement functions and/or operations associated with one of the measuring modules 132 of the concentration measurement system 120 of FIG. 1. In this regard, the concentration measurement system 500 may comprise suitable components, circuitry, logic, interfaces, and/or code that may be operable to generate and/or obtain measurement concentration of particle content in streams (e.g., particles corresponding to extinguishing and/or suppression agents in the fire extinguishing and/or suppression stream), and/or to perform any required analysis thereof, to enable determining whether measured concentrations are indicative of appropriate concentrations and/or levels (e.g., meeting required concentration or certain characteristics, whether as precise value(s) or as being within particular range, for certain substance(s), such as extinguishing and/or suppression agent(s), as mandated by, for example, regulatory guidelines—such as by the FAA regulations for certification purposes).

The concentration measurement system 500 may be configured to measure concentrations of particle content based on counting of particle. In this regard, the concentration measurement system 500 may be operable to implement particle counting based on light obscuration, by measuring light (and thus obscuration levels) using a fiber optic transmitter and receiver for example. The obscuration related measurements may in turn be used to enable determining particle count, and/or distribution or concentration of the material travelling through the concentration measurement system 500, in real time, or at any time or time frequency. In some instances, the measured obscuration levels may be converted to electrical data (voltage or current), and the concentration measurement system 500 may be calibrated to produce concentration levels of the mixture stream, and/or any particles contained therein, as it is routed through the system.

The concentration measurement system 500 may comprise, for example, one or more in-flow tubes 520 and one or more out-flow tubes 530, for use in routing the stream containing the particle through a measurement module 510. The in-flow tubes 520 and/or the out-flow tubes 530 may be used to facilitate the routing of mixture stream through the measurement module 510, substantially as described with respect to the in-flow tubes 140 and/or the out-flow tubes 150 of FIG. 1.

The measurement module 510 may comprise a fiber optic light transmitter 512 and a fiber optic light receiver 514. The fiber optic light transmitter 512 may be configured to transmit light in directed, narrow beams through the mixture stream routed via the concentration measurement system 500, to enable detecting and/or identifying particular particles in the routed mixture stream. In this regard, the fiber optic light receiver 514 may be configured to receive light emitted from the fiber optic light transmitter 512. Accordingly, analyzing the light received via the fiber optic light receiver 514 may enable determining any changes that may occur as result of the light traveling through the routed mixture stream and/or interacting with any material therein (e.g., solid or aerosol extinguishing and/or suppression agents' particles).

For example, an optical to electrical convertor 540 may be configured to measure obscuration levels in the measurement module 510, based on comparison between the light emitted from the fiber optic light transmitted 512 and the light received by the fiber optic light receiver 514. The optical to electrical convertor 540 may then determine corresponding electrical voltage or current, based on the measured obscuration levels. Clear gases, vapors and particles may have colorants added whether in the original extinguishing and/or suppression agent or by controlled injection into the flow tube (520) or into the measurement module (510) to help measure the concentration level.

The concentration measurement system 500 may also comprise an analyzer 550 and/or a computer 560. In this regard, the analyzer 550 and the computer 560 may be substantially similar to the analyzer 260 and the computer 270, respectively, as describe with respect to FIG. 2. The analyzer 550 and/or the computer 560 may be configured to analyze and/or process electrical information, generated by the optical to electrical convertor 540 based on measured obscuration levels, and/or to generate or derive particle count related data therefrom, which may in turn be utilized in calculating concentrations of the particle content. In some instances, the analyzer 550 and/or the computer 560 may be configured to determine whether the measured concentration and/or characteristics of particle content in the routed stream may be indicative of appropriate levels of the particle. This may enable, for example, confirming whether concentration of extinguishing and/or suppression agent(s) in fire extinguishing and/or suppression stream is acceptable.

Figure 6:
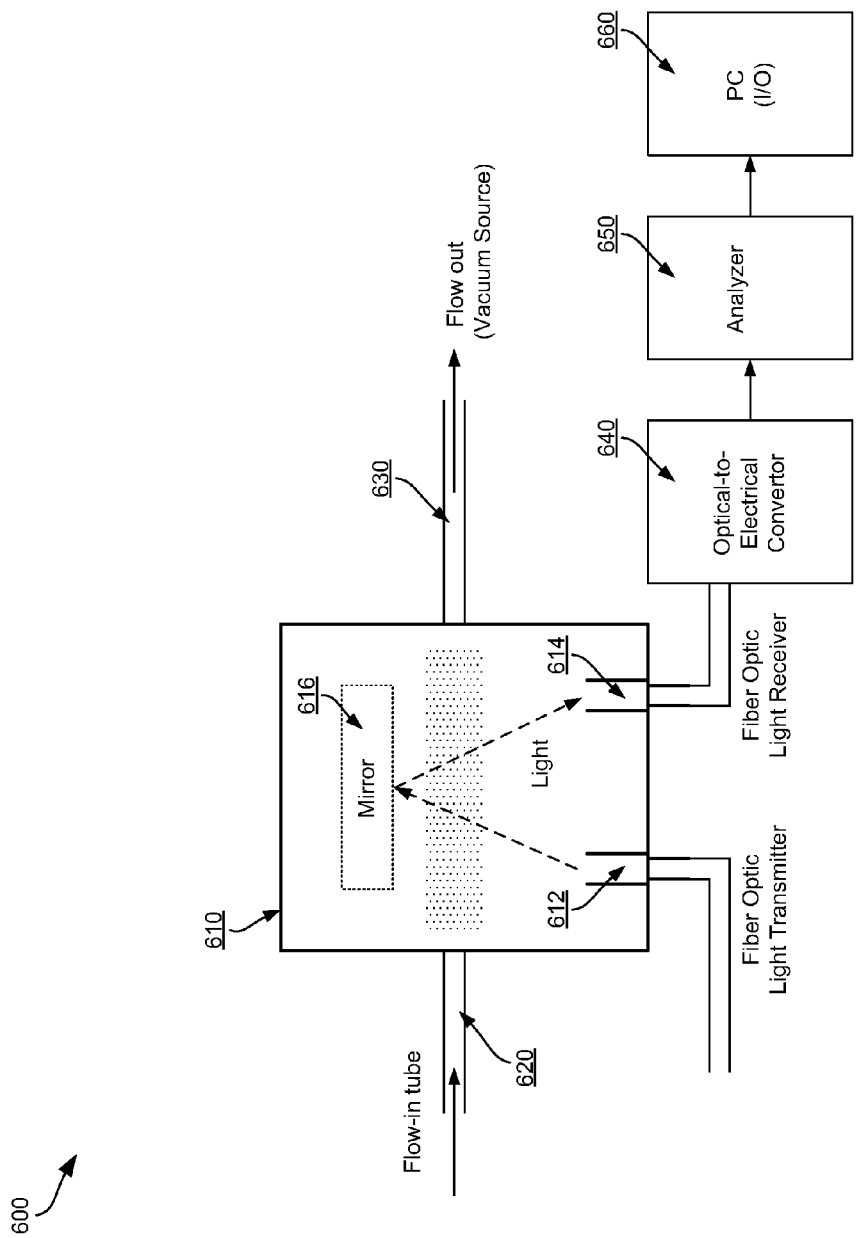
FIG. 6 is a diagram illustrating a particle concentration measurement module that may be utilized in determining concentration of particular agents in a stream based on obscuration or light scattering techniques using a fiber optic light source, in accordance with another advantageous embodiment of the invention.

FIG. 6 is a diagram illustrating a particle concentration measurement module that may be utilized in determining concentration of particular agents in a stream based on obscuration or light scattering techniques using a fiber optic light source, in accordance with another advantageous embodiment of the invention. Referring to FIG. 6, there is shown a concentration measurement system 600.

The concentration measurement system 600 may be substantially similar to the concentration measurement system 500 of FIG. 5, and may similarly be configured to implement particle counting based on obscuration, by measuring light (and thus obscuration levels) using a fiber optic transmitter and receiver for example. The concentration measurement system 600 may also be operable, as described with regard to concentration measurement system 500 of FIG. 5, to utilize the obscuration related measurements in determining particle count, and/or distribution or concentration of the material travelling through the concentration measurement system 600, in real time, or at any time or time frequency.

To that end, the concentration measurement system 600 may comprise, for example, a measurement module 610, one or more in-flow tubes 620 and/or one or more out-flow tubes 630, for use in routing the stream containing the particle through the measurement module 610, an optical to electrical convertor 640, an analyzer 650, and a computer 660. Furthermore, the measurement module 610 may also comprise a fiber optic light transmitter 612 and a fiber optic light receiver 614. Each of the components listed herein may be substantially similar to the corresponding component(s) in the concentration measurement system 500, as described with respect to FIG. 5.

The fiber optic light transmitter 612 and the fiber optic light receiver 614 may be arranged in different manner in the measurement module 610, however. In this regard, rather than being configured to receive light directly from the fiber optic light transmitter 612 (thus requiring them to be aligned perfectly), the fiber optic light receiver 614 may be configured to receive light emitted from the fiber optic light transmitter 612 indirectly, such as by using a mirror 616. In other words, the light received via the fiber optic light receiver 614 would have been emitted by the fiber optic light transmitter 612 and then reflected off the mirror 616, after passing (both in the incident path and the reflected path) through the mixture stream routed through the measurement module 610.

Accordingly, analyzing the light received via the fiber optic light receiver 614 may enable determining any changes that may occur as result of the light traveling through the routed mixture stream and/or interacting with any material therein (e.g., solid or aerosol extinguishing and/or suppression agents' particles), but must also account for the reflection via the mirror 616. Clear gases, vapors and particles may have colorants added whether in the original extinguishing and/or suppression agent or by controlled injection into the flow tube (620) or into the measurement module (610) to help measure the concentration level.

The optical to electrical convertor 640 may then measure obscuration levels in the measurement module 610, and/or may determine corresponding electrical voltage or current, based on the measured obscuration levels. The electrical information may then be provided to the analyzer 650 and/or the computer 660, which may analyze and/or process the electrical information, and/or may generate or derive particle count related data therefrom, which may in turn be utilized in calculating concentrations of the particle content.

In some instances, the analyzer 650 and/or the computer 660 may be configured to determine whether the measured concentration and/or characteristics of particle content in the routed stream may be indicative of appropriate levels of the particle (e.g., meeting required concentration or certain characteristics, whether as precise value(s) or as being within particular range, for certain substance(s), such as extinguishing and/or suppression agent(s), as mandated by, for example, regulatory guidelines—such as by the FAA regulations for certification purposes). This may enable, for example, confirming whether concentration of extinguishing and/or suppression agent(s) in fire extinguishing and/or suppression stream is acceptable.

Figure 7:
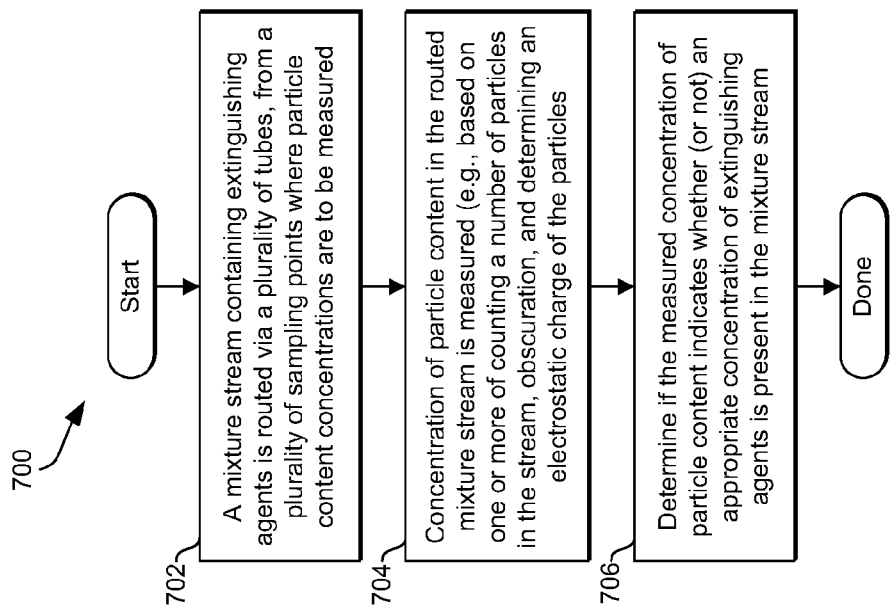
FIG. 7 is a flow chart that illustrates measurement of solid, aerosol, vapor, liquid, liquid particles, or gases, concentration and particle size in stream, in accordance with an advantageous embodiment of the invention.

FIG. 7 is a flow chart that illustrates measurement of solid, aerosol, vapor, liquid, gas particle size and/or concentration in stream, in accordance with an advantageous embodiment of the invention. Referring to FIG. 7, there is shown a flow chart 700 comprising a plurality of steps, which may be applied to measure solid, aerosol, vapor, liquid, gas particle size and/or concentration in streams, such as streams from fire extinguishing and/or suppression components in an aircraft.

In step 702, a plurality of mixture streams containing extinguishing and/or suppression agents may be routed via a plurality of tubes, from a plurality of sampling points where particle content concentrations are to be measured. For example, the in-flow tubes 140 and/or the out-flow tubes 150 may be utilized to force the mixture steams through the measurement component 130 of the concentration measurement system 120, using one or more vacuum sources at the out-flow side for example. In step 704, concentration of particle content in the routed mixture streams may be measured. In this regard, various techniques may be utilized in measuring the concentration of particle content, including, for example, particle counting techniques and/or based on measurement of electrostatic charge of the particles (as described with respect, for example, FIGS. 2-6).

In some instances, in addition to and/or in lieu of calculation concentration of particle content, the measurement process may comprise determining characteristics (e.g., particle size) associated with the particle content (e.g., particle size). In step 706, it may be determined whether the measured concentration of particle content may indicate whether (or not) an appropriate concentration of extinguishing and/or suppression agents may be present in the mixture streams. The process may be performed only once, such as during certification of the fire extinguishing and/or suppression system (or the aircraft containing the fire extinguishing and/or suppression system). In some instances, the process may be repeated, such as periodically and/or on-demand (e.g., whenever the fire extinguishing and/or suppression system is inspected or tested, such as in pre-flight or in-flight testing) or in a continuous mode such as during operation as a fixed system on an aircraft.

Other embodiments of the invention may provide a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the steps as described herein for measurement of solid or aerosol particle size and concentration.

Accordingly, the present invention may be realized in hardware, software, or a combination of hardware and software. The present invention may be realized in a centralized fashion in at least one computer system or in a distributed fashion where different elements are spread across several interconnected computer systems, which may be connected using wired and/or wireless connections. Any kind of computer system or other system adapted for carrying out the methods described herein is suited. A typical combination of hardware and software may be a general-purpose computer system with a computer program that, when being loaded and executed, controls the computer system such that it carries out the methods described herein.

The present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method for measuring particle content, comprising:
routing a plurality of streams, via a plurality of tubes, from a plurality of sampling points where particle content concentrations are to be measured, wherein the plurality of sampling points comprises a plurality of compartments that are fluidly isolated from each other, wherein each sampling point comprises an injector for injecting one or more of an extinguishing agent and a suppression agent at each sampling point, wherein the one or more of the extinguishing agent and the suppression agent injected at one of the sampling points is isolated and independent from the one or more of the extinguishing agent and the suppression agent injected at other sampling points;
separately measuring concentration of particle content in each of the plurality of streams, wherein the measuring is based on one or both of:
counting a number of particles; and
determining an electrostatic charge of the particles; and
determining whether the measured concentration of particle content from each sampling point is indicative of an appropriate concentration of the one or more of the extinguishing agent and the suppression agent at each sampling point.

2. The method of claim 1, comprising providing outputs of at least one of counting of the number of the particles and determining the electrostatic charge of the particles to a computer or analyzer configured to provide a reading for the determination of whether the particle count or electrostatic charge is indicative of an appropriate concentration.

3. The method of claim 1, comprising determining the electrostatic charge based on a determination of a difference in a generated current as the particles pass through at least one sensor.

4. The method of claim 1, comprising counting the number of particles based on one or both of particle image velocemetry, light or laser scattering, and light or laser obscuration.

5. The method of claim 1, comprising repeating the measuring of concentration of particle content at a given frequency.

6. The method of claim 1, wherein the appropriate concentration corresponding with at least two of the plurality of sampling points are different.

7. The method of claim 1, wherein the plurality of streams comprise one or both of a solid agent and an aerosol agent.

8. The method of claim 1, comprising routing the plurality of streams using a vacuum pump.

9. The method of claim 1, comprising routing the plurality of streams after the measuring of concentration of particle content via one or more out-flow tubes.

10. The method of claim 9, wherein at least some of the one or more out-flow tubes are interconnected to a manifold.

11. An apparatus for measuring particle content, comprising:
a plurality of tubes configured for routing a plurality of streams from a plurality of sampling points where particle content concentrations are to be measured, wherein the plurality of sampling points comprise a plurality of areas of an aircraft, wherein each area of the plurality of areas of the aircraft is fluidly isolated from other areas of the plurality of areas of the aircraft, wherein each sampling point comprises an injector for injecting one or more of an extinguishing agent and a suppression agent at each sampling point, wherein the one or more of the extinguishing agent and the suppression agent injected at one of the sampling points is isolated and independent from the one or more of the extinguishing agent and the suppression agent injected at other sampling points;

a measuring component comprising a plurality of sensors, each sensor configured to separately measure a concentration of particle content in a respective one of the plurality of streams, wherein each sensor measures the concentration of particle content based on one or both of:
  counting a number of particles; and
  determining an electrostatic charge of the particles; and
an analyzer configured for determining whether the measured concentration of particle content from each sampling point is indicative of an appropriate concentration of one or more of an extinguishing and a suppression agent at each sampling point.

12. The apparatus of claim 11, wherein measuring component comprises at least one measurement module that comprises at least one sensor that is operable to determine an electrostatic charge of the particles as the particles pass through the at least one sensor.

13. The apparatus of claim 12, wherein the at least one measurement module is configured to determine the electrostatic charge based on determining of a difference in a generated current as the particles pass through the at least one sensor.

14. The apparatus of claim 11, wherein the measuring component comprises at least one measurement module that comprises:
  at least one source; and
  at least one counter for counting the number of particles based on an emission from the one source.

15. The apparatus of claim 14, wherein the at least one source comprises a fiber optic light source or a laser source, and the at least one counter is configured to count the number of particles based on at least one of scattering and obscuration of transmitted light or laser.

16. The apparatus of claim 14, wherein the at least one source comprises a light source or a laser source, and the at least one counter is configured to count the number of particles based on particle image velocemetry.

17. The apparatus of claim 11, wherein the measuring component is configured to repeat the measuring of concentration of particle content at a given frequency.

18. The apparatus of claim 11, wherein the appropriate concentration corresponding with at least two of the plurality of sampling points are different.

19. The apparatus of claim 11, wherein the plurality of streams comprise one or both of a solid agent and an aerosol agent.

20. The apparatus of claim 11, comprising a vacuum pump for routing the plurality of streams into the measuring component.

21. The apparatus of claim 11, comprising one or more out-flow tubes configured for routing the plurality of streams from the measuring component after the measuring of concentration of particle content.

22. An apparatus for measuring particle content, comprising:
  a plurality of tubes configured for routing a plurality of streams from a plurality of sampling points where particle content concentrations are to be measured, wherein each sampling point comprises an injector for injecting one or more of an extinguishing agent and a suppression agent at each sampling point, wherein the one or more of the extinguishing agent and the suppression agent injected at one of the sampling points is isolated and independent from the one or more of the extinguishing agent and the suppression agent injected at other sampling points;
  a measuring component configured for separately measuring each concentration of particle content in each of the plurality of streams based on one or both of:
    counting a number of particles; and
    determining an electrostatic charge of the particles; and
  an analyzer configured for determining whether the measured concentration of particle content from each sampling point is indicative of an appropriate concentration of the one or more of the extinguishing and the suppression agent at each sampling point, wherein the appropriate concentration corresponding with at least two of the plurality of sampling points are different.

* * * * *

UNITED STATES PATENT AND TRADEMARK OFFICE
CERTIFICATE OF CORRECTION

PATENT NO. : 9,182,331 B2
APPLICATION NO. : 13/600745
DATED : November 10, 2015
INVENTOR(S) : Sham S. Hariram It is certified that error appears in the above-identified patent and that said Letters Patent is hereby corrected as shown below:

Specification

Column 2, Line 47
"particle image velocemetry"---should read "particle image velocimetry"

Column 3, Line 29
"image velocemetry (PIV) based techniques"---should read "image velocimetry (PIV) based techniques"

Column 4, Line 59
"particle image velocemetry"---should read "particle image velocimetry"

Column 12, Line 67
"image velocemetry (PIV) based techniques"---should read "image velocimetry (PIV) based techniques"

Column 13, Line 21
"using velocemetry based techniques"---should read "using velocimetry based techniques"

Column 13, Line 23
"particle image velocemetry"---should read "particle image velocimetry"

Column 13, Line 24
"laser Doppler velocemetry"---should read "laser Doppler velocimetry"

Column 13, Line 25
"particle tracking velocemetry"---should read "particle tracking velocimetry"

Signed and Sealed this
Twenty-second Day of March, 2016

Michelle K. Lee
*Director of the United States Patent and Trademark Office*

CERTIFICATE OF CORRECTION (continued)
U.S. Pat. No. 9,182,331 B2

Specification

Column 13, Line 26
        "In velocemetry based techniques"---should read "In velocimetry based techniques"

Column 13, Line 56
        "based on velocemetry techniques"---should read "based on velocimetry techniques"

Column 13, Line 65
        "process velocemetry related measurements"---should read "process velocimetry related measurements"

Column 13, Line 66
        "velocemetry data obtained"---should read "velocimetry data obtained"

Claims

Column 18, Line 41, Claim 4
        "particle image velocemetry"---should read "particle image velocimetry"

Column 19, Line 44, Claim 16
        "particle image velocemetry"---should read "particle image velocimetry"